United States Patent
Menges et al.

(10) Patent No.: US 9,568,414 B2
(45) Date of Patent: Feb. 14, 2017

(54) MICROPLATE READER WITH LID LIFTER FOR MICROPLATES

(71) Applicant: TECAN TRADING AG, Mannedorf (CH)

(72) Inventors: Friedrich Menges, Berchtesgaden (DE); Harald Gebetsroither, Grodig (AT); Gyoergy Wenczel, Seekirchen (AT)

(73) Assignee: TECAN TRADING AG, Mannedorf (CH)

( * ) Notice: Subject to any disclaimer, the term of this patent is extended or adjusted under 35 U.S.C. 154(b) by 0 days.

(21) Appl. No.: 14/697,012

(22) Filed: Apr. 27, 2015

(65) Prior Publication Data

US 2015/0233815 A1    Aug. 20, 2015

Related U.S. Application Data

(63) Continuation-in-part of application No. 13/956,551, filed on Aug. 1, 2013, now Pat. No. 9,029,101.

(30) Foreign Application Priority Data

Aug. 9, 2012  (CH) .................................... 1306/12

(51) Int. Cl.
| | |
|---|---|
| *G01N 21/01* | (2006.01) |
| *G01N 21/63* | (2006.01) |
| *G01N 21/76* | (2006.01) |
| *G01N 21/64* | (2006.01) |
| *G01N 21/03* | (2006.01) |

(52) U.S. Cl.
CPC ...... *G01N 21/0303* (2013.01); *G01N 21/6428* (2013.01); *G01N 21/76* (2013.01); *G01N 2201/022* (2013.01); *G01N 2201/0446* (2013.01)

(58) Field of Classification Search
None
See application file for complete search history.

(56) References Cited

U.S. PATENT DOCUMENTS

| | | |
|---|---|---|
| 6,449,827 B1 | 9/2002 | Clarke et al. |
| 7,666,362 B2 | 2/2010 | Shanler |
| 2011/0220239 A1* | 9/2011 | Reed .................... B01L 3/5025 141/1 |
| 2011/0293488 A1 | 12/2011 | Nichols et al. |

FOREIGN PATENT DOCUMENTS

| | | |
|---|---|---|
| DE | 201 01 734 | 7/2002 |
| DE | 202004009793 U1 * | 8/2004 .......... B01L 3/50851 |
| EP | 0 114 259 | 8/1984 |
| EP | 1 192 995 | 4/2002 |
| EP | 1 640 723 | 3/2006 |
| WO | WO 93/08914 | 5/1993 |

OTHER PUBLICATIONS

Eng. translation of Quantifoil Instruments. German Patent Application Publication No. DE 20 2004 009 793 U1. Date of Publication: Aug. 19, 2004. Biological reaction chamber for e.g., microarrays, microtitration plates and slides, includes permanent magnets in lid and walls. pp. 1-5.*

* cited by examiner

*Primary Examiner* — Renee Claytor
*Assistant Examiner* — Sharon M Papciak
(74) *Attorney, Agent, or Firm* — Notaro, Michalos & Zaccaria P.C.

(57) ABSTRACT

Microplate reader has a housing, at least one optical measuring/detection device, a microplate support, a moving unit and an integrated lid holding apparatus. The lid holding apparatus moves the microplate in one respective, at least approximately vertical direction for moving the microplate lid away from the microplate. The lid holding apparatus is arranged inside the housing as a magnetic lifter and comprises a non-array arrangement of at least one permanent magnet, or at least three electro magnets, or at least one switchable permanent magnet. Each microplate lid to be moved away from the microplate comprises magnetizable material with a physical area. A projected area of the at least one permanent magnet, electro magnet, or switchable permanent magnet is smaller than the physical area of the magnetizable material of the microplate lid.

9 Claims, 7 Drawing Sheets

Fig. 15
Fig. 16
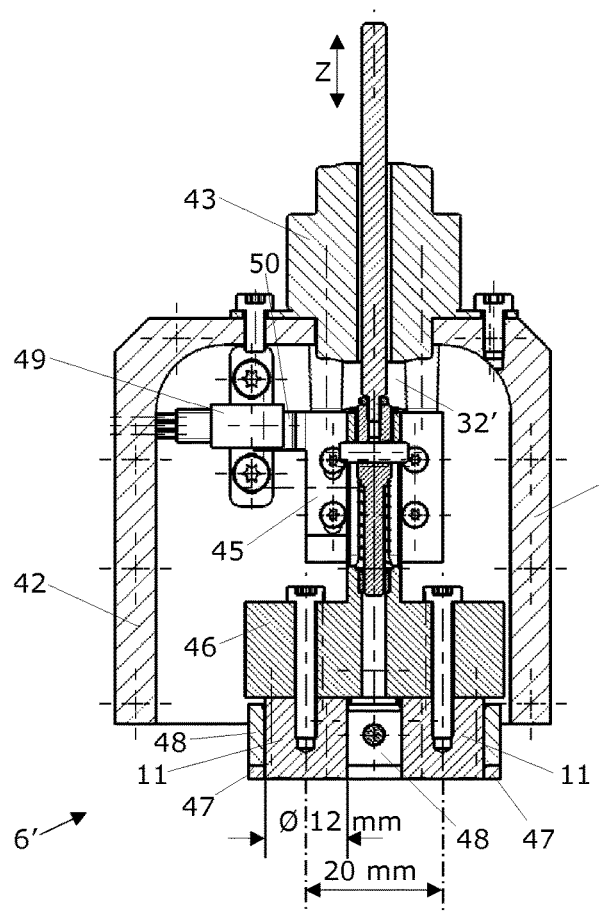
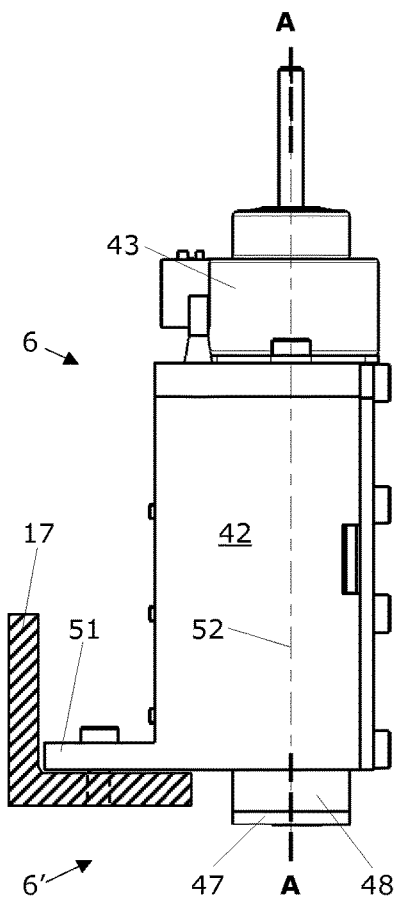
Fig. 17
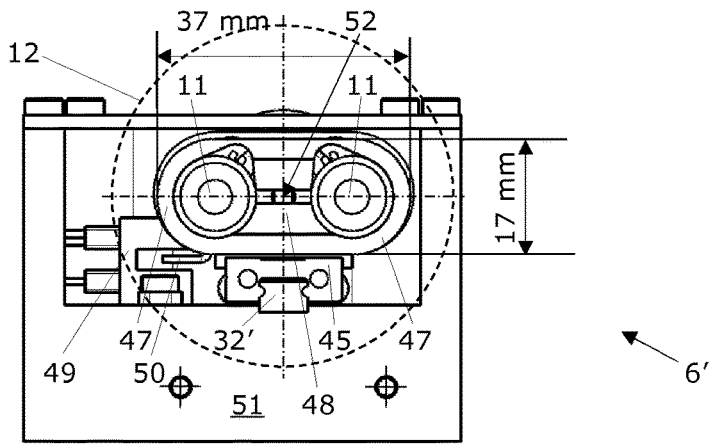

MICROPLATE READER WITH LID LIFTER FOR MICROPLATES

RELATED PATENT APPLICATIONS

This patent application is a continuation-in-part application of U.S. Ser. No. 13/956,551, that has been filed on Aug. 1, 2013, published as US 2014/0045210 A1 and is now U.S. Pat. No. 9,029,101 issued May 12, 2015, and that claims priority of the Swiss patent application No. CH 01306/12 filed on Aug. 9, 2012. The entire content of both applications is incorporated herein by explicit reference.

RELATED FIELD OF TECHNOLOGY

The invention relates to a lid lifter for microplates which is installed in a microplate reader with at least one optical measuring/detection device. Microplates allow for example performing biological or biochemical tests in which a large number of samples are processed in parallel. Microplate readers have proven their worth in the optical evaluation of test results that are achieved in microplates.

All multi-well plates are designated as microplates in connection with the present invention which comprise a plurality of wells or containers which are arranged in an array. Especially preferred microplates at least approximately have the dimensions and footprint of a microplate according to the SBS standard, as published by the American National Standards Institute (ANSI). Microplates are known for example whose wells are provided with a round base, flat base or V bottom. The wells can be arranged as normal wells or deep wells. Wells in the form of a truncated cone or a truncated pyramid are known as well. It is a common feature in all microplates with different kinds of well shapes that they have a standardized base area, i.e. a standardized footprint, and that the axial distance of the wells respectively arranged in an orthogonal array is also standardized. This axial distance is 18 mm in 24 well (4×6) plates, 9 mm in 96 well (8×12) plates, 4.5 mm in 384 well (16×24) plates, and 2.25 mm in 1536 well (32×48) plates. The height of a microplate can vary strongly depending on the type thereof and is typically between 10.4 mm (e.g. 1536 V base deep well plate) and 44 mm (e.g. 96 well Masterblock® of Greiner).

If biological or biochemical tests are performed in microplates over a prolonged period of time (over hours or even days) and/or at temperatures increased over room temperature, evaporation occurs often and typically, which can lead to a decrease in volume and changes in concentration of electrolytes and macromolecules up to drying up of the samples. For this reason, the microplates are preferably processed in a separate incubator, wherein the temperature and the air humidity are controlled in such a way that no evaporation will occur. It is disadvantageous that the microplates need to be transferred back and forth manually between the incubator and the reader. This discussion relates to the operation as a standalone reader. If the reader is a part of a robotic system on the other hand (larger laboratory installations, especially automated laboratory systems, usually comprise a robot which is usually provided with pipette tips for the transport of fluids or with grippers for the transport of laboratory items such as microplates or sample tubes; Freedom EVO® Liquid Handling Workstation of the current applicant can be mentioned as an example for such a laboratory system), the robot of this system assumes the transfer between the reader and the multiple incubator. The microplates could be processed alternatively in the reader itself, with the advantage that measuring cycles can be performed in between and automatically. It however would be disadvantageous in a robotic system to block a reader with a single microplate for days.

The evaporation of sample fluid from microplates is combated as a standard in such a way that the microplate is covered by a lid or that the microplate or its wells are sealed with self-adhesive or laminated foils. Such covering or closing leads to a number of disadvantages such as:

- the use of a robotized injector for adding agents to the wells (e.g. for triggering luminescence reactions in the samples) is not possible;
- the covering reduces the gas supply from the ambient environment to the wells, thereby leading to a deficiency in oxygen and/or carbon dioxide in the wells, which depending on the type of the cell will slow down cell growth, extend processing time and reduce the maximum achievable cell concentrations;
- the gas exchange between the samples in the wells and the ambient environment is reduced or prevented, so that hazardous gas concentrations may form in the air space of the wells above the samples (e.g. in cell cultures or cell-based tests);
- fluid evaporated from the samples may condensate on the bottom side of the lid or the self-adhesive foil, so that the condensation formed thereby will lead to erroneous optical measurements (e.g. the absorbance);
- the lid and the self-adhesive foil will prevent or at least obstruct the optical detection of fluorescence in the samples by means of the preferred top detection (i.e. from above);
- the lid and the self-adhesive foil will prevent the optical detection of luminescence in the samples by means of top detection.

Such problems were prevented at least partly until now in that the lid or the self-adhesive foil was removed before the insertion of a microplate into the microplate reader and the lid or the self-adhesive foil were mounted again after the termination of the measurement or the optical evaluation of the plate in the reader. It is obvious that such manipulations on microplates charged with sensitive samples is laborious and may even be potentially extremely damaging to the samples. In particular, cross contaminations may occur when re-mounting previously used self-adhesive foils. This is especially the case when in the course of a test protocol covering several days the same microplate is to be examined several times and at different times in the microplate reader. Furthermore, accidents cannot be excluded on the way between the location of the removal of the lid or the self-adhesive foil and the location of the microplate reader.

RELATED PRIOR ART

Solutions for the robotized removal of microplate lids are known from the state of the art:

The document US 2011/0293488 A1 for example discloses a specialized lid manipulation apparatus for the automatic lifting of a lid from a microplate or the placement of a lid thereon. The apparatus comprises a horizontally displaceable microplate support which can be moved out of the apparatus and can be equipped with a covered microplate. After the return of the microplate into the apparatus, a horizontally and vertically displaceable lid pressing apparatus will be placed above the microplate and lowered. After unlocking the special lid of the microplate, the lid will be lifted with a suction cup or alternatively with a robotic gripper. The microplate uncovered in this manner will subsequently be moved out of the apparatus together with the microplate support. The task of removing or placing the lid is performed in a relatively complex way. Furthermore, the use of this specialized lid manipulation apparatus requires a change or adjustment of the microplates to be used and the use of special lids.

The document U.S. Pat. No. 7,666,362 B2 describes the production and the use of a special microplate/lid combination, which can be handled by means of a robotic gripper.

Although the advantage of the uncovering of the multi-well plate with the lid is recognized (reduction in the sample evaporation) and the person skilled in the art is obviously aware of robotic removal, the user must use these special microplates and lids and cannot use standard microplates and standard microplate lids.

The document EP 1 192 995 A2 discloses a special lid for standard microplates comprising a seal and a robotic gripper for holding the microplate and for the repeated removal and replacement of this special lid. The lid exerts a spring pressure on the seal, so that it is sealingly connected to the microplate. The robotic gripper is arranged to release the resilient parts of the lid according to this special lid construction and is arranged in a relatively complicated way. Although the user can use standard microplates, standard microplate lids cannot be used.

The document U.S. Pat. No. 6,449,827 B1 discloses a suction mechanism for tightly holding a microplate during the time of the removal of a microplate lid by means of a robotized gripper mechanism.

The document DE 201 01 734 U1 discloses a plate lifter or lid lifter which is equipped with one or two electro magnets that interact with one or two holding elements that are situated on a plate or lid. These holding elements guide the magnetic field that is induced by the electro magnet(s). The distance between two holding elements is equal to the distance between two electro magnets, thus precise alignment of the plate lifter or lid lifter with respect to the plate or lid to be lifted is imperative.

Even though the possibility is partly disclosed to use standard microplates and optionally even standard microplate lids, all known documents of the state of the art do not offer any solution to the problem of the frequently sensitive path of the microplate (and especially the uncovered samples) for the time between the lifting of the lid and the optical analysis of the samples in the microplate reader.

OBJECT AND SUMMARY OF THE PRESENT INVENTION

It is therefore the object of the present invention to propose an alternative apparatus and an alternative method which eliminates the disadvantages known from the state of the art.

This object is achieved according to a first aspect with a microplate reader according to the features as herein disclosed. This microplate reader comprises at least one optical measuring/detection device, a housing, a microplate support and a moving unit. The moving unit is arranged to move the microplate support out of the housing, into the housing and in at least one substantially horizontal direction within the housing. The microplate reader in accordance with the invention is characterized in that it comprises an integrated lid holding apparatus arranged within the housing for moving a microplate lid away from a microplate positioned on the microplate support. The lid holding apparatus is arranged to move the microplate lid and/or the microplate support is arranged to move the microplate in one respective, at least approximately vertical direction. The lid holding apparatus is arranged as a magnetic lifter and comprises a non-array arrangement of at least one:
(i) permanent magnet, or
(ii) electro magnet, or
(iii) switchable permanent magnet.

Each microplate lid to be moved away from the microplate comprises magnetizable material with a physical area, a projected area of the at least one permanent magnet, electro magnet, or switchable permanent magnet being smaller than the physical area of the magnetizable material of the microplate lid.

Preferably, the projected area of the at least one permanent magnet, electro magnet, or switchable permanent magnet is less than a half of the physical area of the magnetizable material of the microplate lid.

This object is achieved according to a second aspect by a method for optically measuring samples in wells of a microplate provided with a microplate lid in such a microplate reader as herein disclosed. The measuring method in accordance with the invention comprises the following steps:
(a) placing the microplate covered by the microplate lid on the microplate support of the microplate reader, the microplate lid comprising magnetizable material;
(b) retracting the microplate support and the covered microplate with the moving unit into the housing of the microplate reader;
(c) moving the microplate lid away from the microplate positioned on the microplate support with a lid holding apparatus integrated in the microplate reader and arranged within the housing;
(d) measuring samples in wells of the microplate with the lifted microplate lid by the at least one optical measuring/detection device,
wherein the lid holding apparatus is arranged as a magnetic lifter and comprises a non-array arrangement of at least one:
(i) permanent magnet, or
(ii) electro magnet, or
(iii) switchable permanent magnet,
and wherein each microplate lid to be moved away from the microplate comprises magnetizable material with a physical area, a projected area of the at least one permanent magnet, electro magnet, or switchable permanent magnet being smaller than the physical area of the magnetizable material of the microplate lid.

Preferably, a microplate lid utilized for carrying out the method comprises magnetizable material with a physical area that is at least double the projected area of the at least one permanent magnet, electro magnet, or switchable permanent magnet of the magnetic lifter.

Further preferred and inventive features are provided in the respective dependent claims.

Advantages of the microplate reader or measuring method in accordance with the invention comprise the following:
  All known measuring methods (e.g. absorbance, fluorescence, luminescence) can be applied to lid-free or covered microplates, while the microplate can be covered by a lid outside of the measuring periods;
  standard microplates and (optionally slightly modified) standard microplate lids can be used;
  in the case of cell-based tests the protection from evaporation by covering can be combined with the provision of sufficient gas exchange by brief exposure of the microplates;

automated injecting of agents (e.g. triggering luminescence or other reactions) is possible while performing tests in lid-protected microplates;

lifting and replacement of the microplate lid allows the performance of long-term tests and the monitoring of long-term kinetics of cell cultures in the wells of microplate;

optical measurements on the samples can be performed sporadically and repeatedly by brief lifting and replacement of the microplate lid;

addition of culture medium or other substances and agents to the cell cultures in the wells of microplate is enabled by brief lifting and replacement of the microplate lid 7.

BRIEF INTRODUCTION OF THE ATTACHED DRAWINGS

An exemplary microplate reader in accordance with the invention will be shown by reference to schematic diagrams. These diagrams shall document selected embodiments of the microplate reader in accordance with the invention, which do not limit the scope of the present invention. It is shown in:

FIG. 1 a vertical sectional view through a microplate reader with extended moving unit and microplate support, after the manual or robotized positioning of a covered microplate on the microplate support;

FIG. 2 a vertical sectional view through a microplate reader with retracted moving unit and microplate support, prior to the lifting of the microplate lid with an integrated lid holding apparatus according to a first embodiment;

FIG. 3 a vertical sectional view through a microplate reader with retracted moving unit and microplate support, during lifting of the microplate lid with a magnetic lifter of the integrated lid holding apparatus according to the first embodiment;

FIG. 4 a vertical sectional view through a microplate reader with retracted moving unit and microplate support, wherein the microplate with lifted microplate lid is ready for measurement;

FIG. 5 a vertical sectional view through a microplate reader with retracted moving unit and microplate support during optical measurement of the microplate with lifted microplate lid and with corrected working distance to the measuring/detection device;

FIG. 6 a vertical sectional view through a microplate reader with retracted moving unit and microplate support during placement of the microplate lid on the microplate;

FIG. 7 a vertical sectional view through a microplate reader with retracted moving unit and microplate support during the movement away of the re-covered microplate by the magnetic lifter of the integrated lid holding apparatus according to the first embodiment;

FIG. 8 a vertical sectional view through a microplate reader with extended moving unit and microplate support during manual or robotized removal of the re-covered microplate from the microplate support;

FIGS. 9A-9D top views of standard microplate lids modified with self-adhesive iron foil, wherein FIG. 9A shows two narrow, transversely disposed and extremely positioned strips on the lid for a 96 well microplate;

Figure 10:
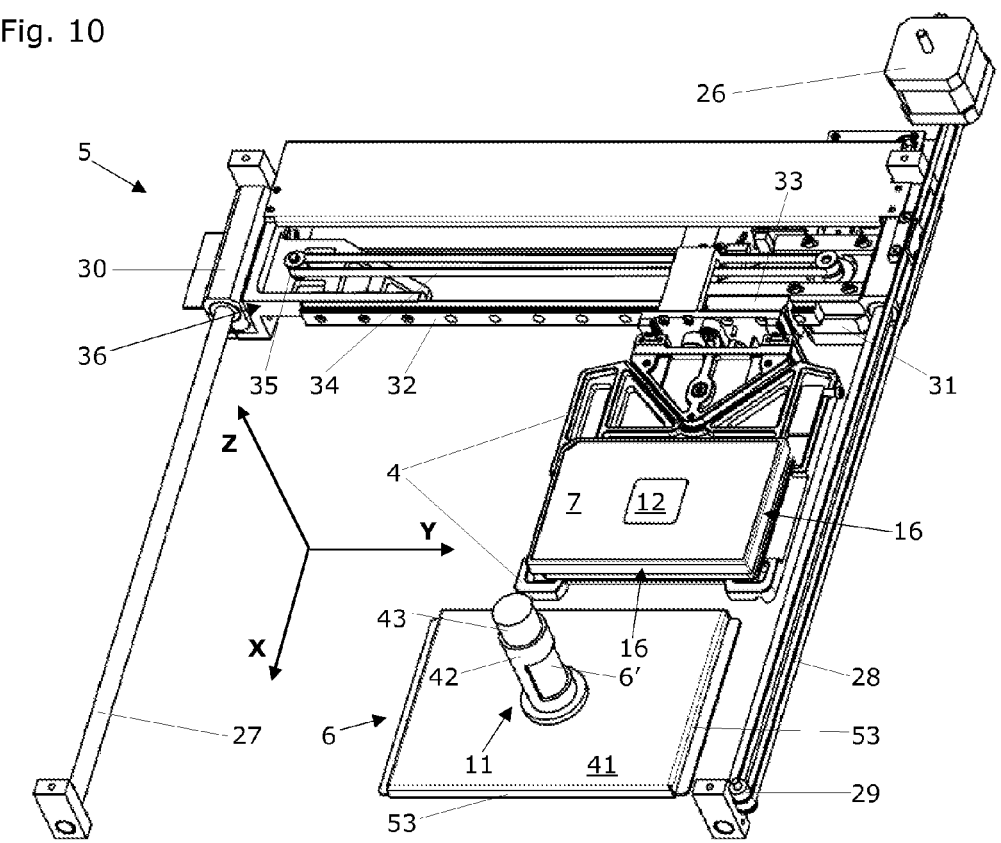
Figure 11:
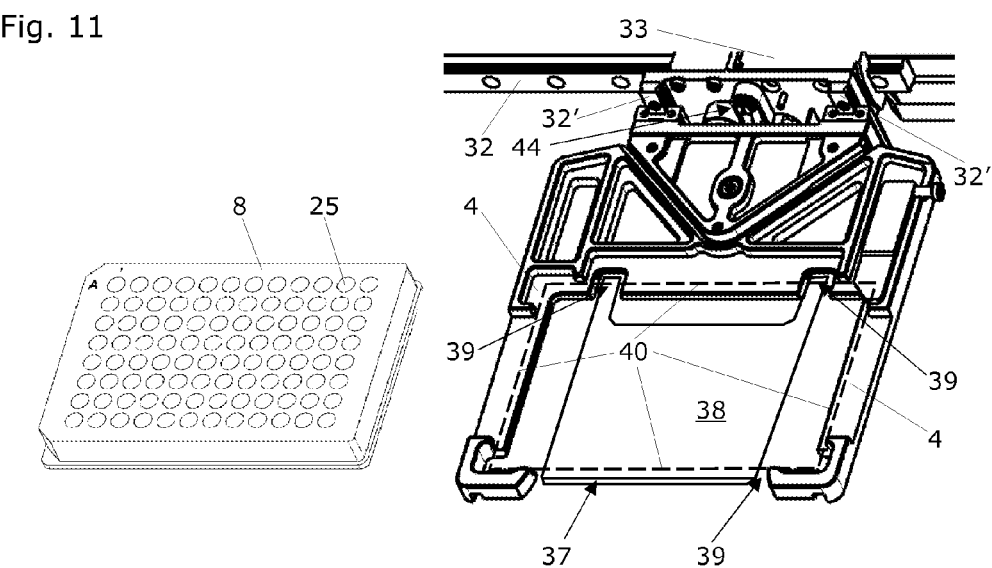
Figure 12:
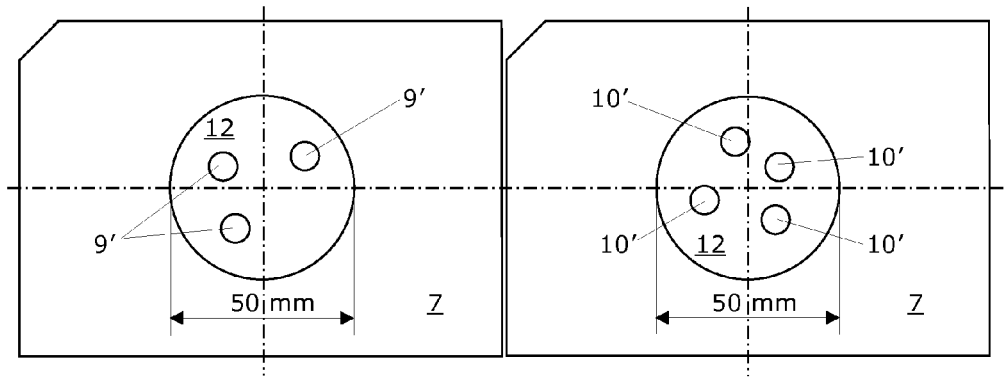
Figure 13:
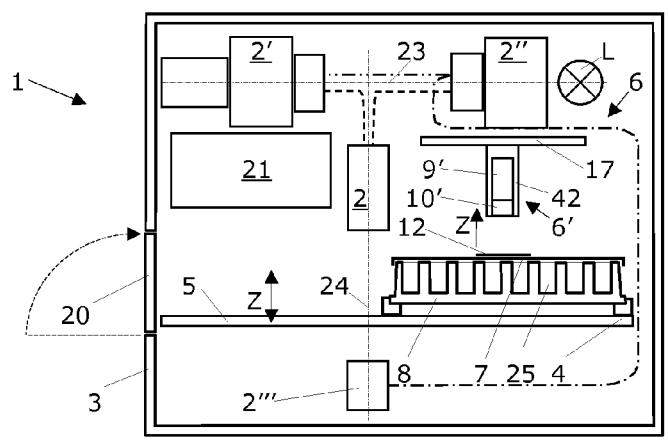
Figure 14:
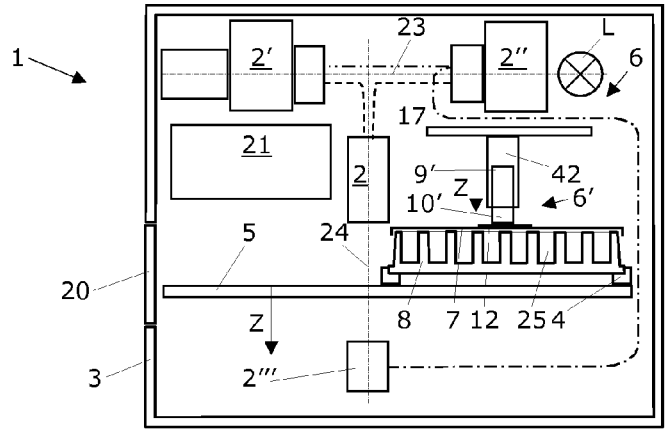
Figure 18A:
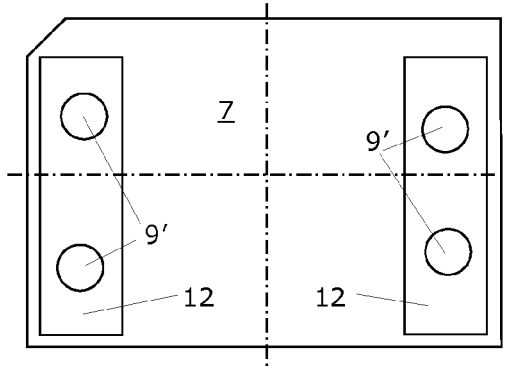
Figure 18B:
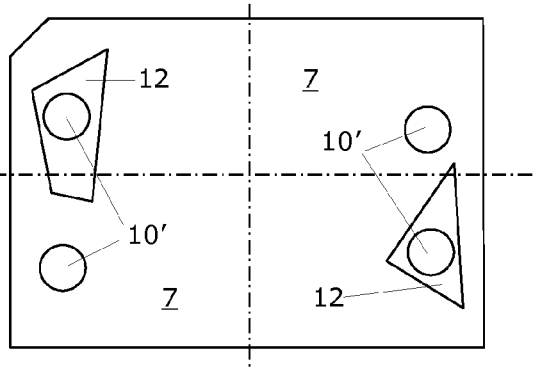
Figure 19A:
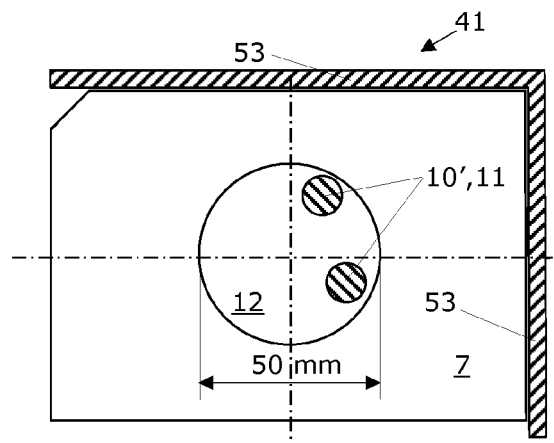
Figure 19B:
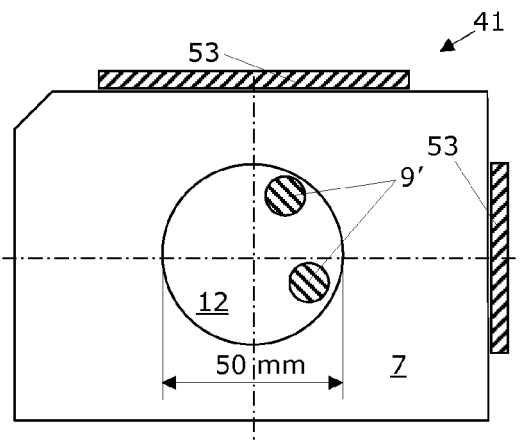
Figure 20A:
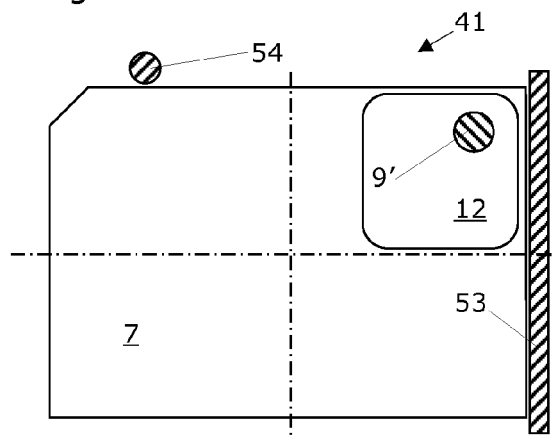
Figure 20B:
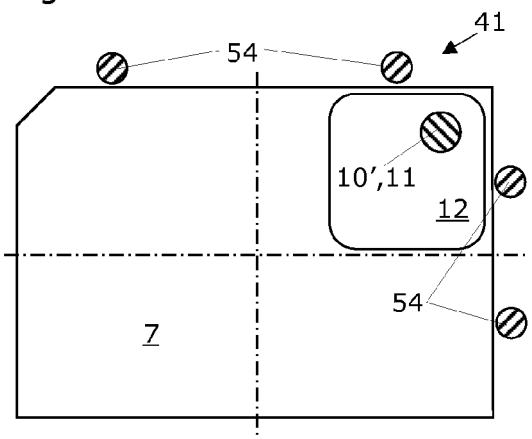

FIG. 10 a 3D view of the moving unit with a microplate with fitted microplate lid, which microplate is positioned on the microplate support;

FIG. 11 a slightly enlarged 3D view of the empty microplate support of the moving unit at a transfer station and in the respective enlargement a 3D view of a 96 well microplate without microplate lid;

FIG. 12 examples of non-array arrangements of three permanent magnets and four electro magnets in relation to the area of a preferred magnetizable material that is attached to a microplate lid;

FIG. 13 a vertical sectional view through a microplate reader with retracted moving unit and microplate support, prior to the lifting of the microplate lid with an integrated lid holding apparatus according to a second embodiment;

FIG. 14 a vertical sectional view through a microplate reader with retracted moving unit and microplate support, during lifting of the microplate lid with a magnetic lifter of the integrated lid holding apparatus according to the second embodiment;

FIG. 15 a vertical section view of the magnetic lifter of the integrated lid holding apparatus according to the second embodiment;

FIG. 16 side view of the magnetic lifter of the integrated lid holding apparatus according to the second embodiment;

FIG. 17 a bottom view of the magnetic lifter of the integrated lid holding apparatus according to the second embodiment;

FIGS. 18A-18B top views of standard microplate lids modified with self-adhesive iron foil, wherein FIG. 18A shows on the lid for a 96 well microplate two identical, transversely disposed strips, each configured to interact with two permanent magnets;

FIG. 18B shows on the lid for a 24 well microplate two transversely positioned, at least approximately triangular pieces configured to interact with one or two electro magnets;

FIGS. 19A-19B a horizontal section view through a crank of a magnetic lifter and a top view of a microplate lid, wherein FIG. 19A shows a crank comprising two guiding flanks that are building a corner and a microplate lid with a centrally positioned magnetizable material configured to interact with two electro magnets or switchable permanent magnets arranged peripherally with respect to the physical area of the magnetizable material;

FIG. 19B shows a crank comprising two guiding flanks that are not touching each other and a microplate lid with a centrally positioned magnetizable material configured to interact with two permanent magnets arranged peripherally with respect to the physical area of the magnetizable material;

FIGS. 20A-20B a horizontal section view through a crank of a magnetic lifter and a top view of a microplate lid, wherein FIG. 20A shows a crank comprising one guiding flank and one guiding pin and a microplate lid with a peripherally positioned magnetizable material configured to interact with one permanent magnet peripherally arranged with respect to the physical area of the magnetizable material;

FIG. 20B shows a crank comprising guiding pins on two sides and a microplate lid with a peripherally positioned magnetizable material configured to interact with one electro magnet or switchable permanent magnet arranged peripherally with respect to the physical area of the magnetizable material.

DETAILED DESCRIPTION OF THE PRESENT INVENTION

Figure 1:
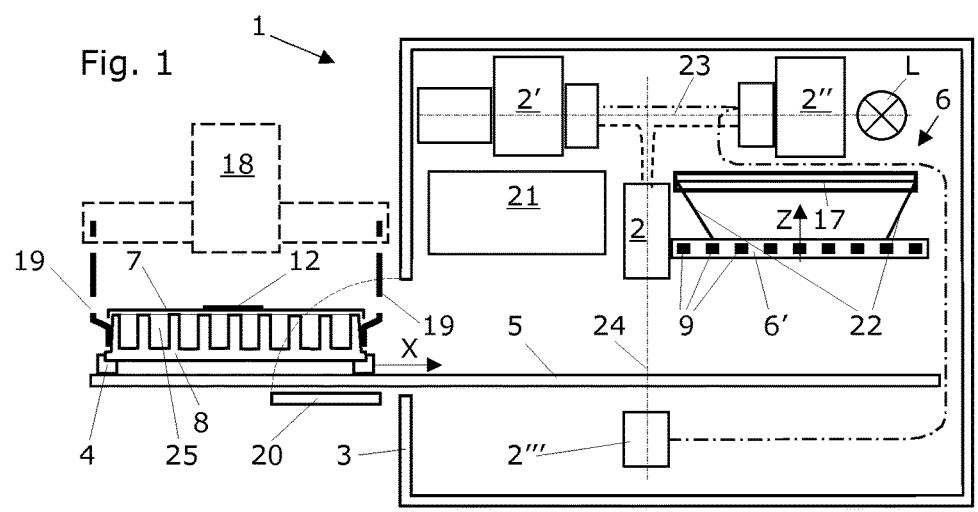

FIG. 1 shows a vertical sectional view through a microplate reader 1 with extended moving unit 5 and microplate support 4, after the manual or robotized positioning of a covered microplate 8 on the microplate support 4. The microplate reader 1 comprises a control unit 21 for monitoring and checking the functions of the reader and the moving unit 5.

The microplate reader 1 as shown here comprises at least one optical measuring/detection device 2. The microplate reader 1 further comprises a housing 3, a microplate support 4 and a moving unit 5, wherein the moving unit 5 is arranged to move the microplate support 4 out of the housing 3, into the housing 3 and, within the housing 3, in at least one substantially horizontal direction. The housing 3 is preferably optically sealed against the ambient environment. The housing can also be insulated with respect to the temperature, the gas composition and its relative humidity against the ambient environment and can therefore be arranged as a climatic chamber.

This optical measuring/detection device 2 can also be referred to as a "measuring head" and can be fixed in a stationary manner, i.e. in an immobile way. In this case, the moving unit 5 is additionally arranged in a height-movable way for focusing the optical measuring/detection device 2. Alternatively, the optical measuring/detection device 2 can be arranged in a height-displaceable manner, so that it can be moved from a parking position to a measuring position for example, wherein such a measuring head 2 preferably comprises at least one fine Z drive which is arranged to focus the optical measuring/detection device 2. A further alternative comprises the arrangement of a height-movable optical measuring/detection device 2 and a height-movable moving unit 5. For the purpose of focusing the optical measuring/detection device 2, the measuring head 2 will preferably be equipped in this case with a fine Z drive for focusing the optical measuring/detection device.

The microplate reader 1 further comprises an integrated lid holding apparatus 6 arranged within the housing 3 for lifting a microplate lid 7 from a microplate 8 positioned on the microplate support 4 and for placing a microplate lid 7 on a microplate 8. Preferably, the lid holding apparatus 6 is arranged to lift a microplate lid 7 from a microplate positioned on the microplate support 4 for holding said microplate lid 7 during the optical measurement of the microplate 8 and for placing said microplate lid 7 on the same microplate 8. It can alternatively be provided that the lid holding apparatus 6 is arranged in such a way that the microplate lid 7 can be placed within the housing 3 of the microplate reader 1 during the measurement of the microplate 8.

For the purpose of moving the microplate lid 7 away from the microplate 8, the lid holding apparatus 6 and/or the microplate support 4 can be arranged to be moved in one respective, approximately vertical direction. As a result, either the microplate lid 7 is lifted from the microplate 8, or the microplate 8 is lowered in relation to the microplate lid 7. A third possibility is the moving of the microplate lid 7 and the microplates 8 away from each other.

The exemplary microplate reader 1 as shown in FIGS. 1 to 8 comprises a lid holding apparatus 6 which is arranged as a magnetic lifter 6' according to a first embodiment. Said lid holding apparatus 6 preferably comprises an array of permanent magnets 9. Such arrays may be orthogonal, hexagonal or any other non-linear but regular arrangement or distribution. Said lid holding apparatus 6 is fixed here by means of flexible or pliable elements 22 to a carrying apparatus 17. Said flexible or pliable elements 22 are preferably attached in such a way (as illustrated) that their fixing locations on the carrying apparatus 7 are situated further apart than their fastening members on the magnetic lifter 6'. This arrangement automatically leads to an effective self-centering of the magnetic lifter 6' and additionally efficiently dampens its natural oscillations. The carrying apparatus 17 must therefore be arranged in a respectively cantilevered manner. These flexible or pliable elements 22 are preferably arranged as cords or ropes comprising metal. The illustrated carrying apparatus 17 is arranged in a height-adjustable way, wherein any movements are respectively indicated with a directional arrow and a "Z".

Alternatively, the lid holding apparatus 6 preferably comprises an electromagnetic array 10 (not shown) or an individual switchable permanent magnet 11 (see FIG. 10). Such arrays may be orthogonal, hexagonal or any other non-linear but regular arrangement or distribution. It is preferable in each of these cases that each microplate lid 7 to be lifted and placed comprises magnetizable material 12. The magnetizable material 12 is preferably chosen from a group which comprises self-adhesive metal foils, applied metallic lacquers, insert-molded metallic chips or metallic grains, and metal plates or metal foils that are insert-molded or back-molded with plastics. The metals are preferably chosen from the group which comprises iron, nickel, cobalt and their alloys, and alloys of these metals with non-magnetizable metals.

The exemplary microplate reader 1 shown in FIG. 1 further comprises an optical axis 23 which is arranged in a substantially horizontal way and a detection axis 24 which is arranged in a substantially vertical way. On the optical axis 23 and above the moving unit 5, arranged with the microplate support 4, said microplate reader 1 comprises detection optics 2', a light source L and first excitation optics 2". Furthermore, this microplate reader 1 comprises second excitation optics 2''', which is arranged beneath the moving unit 5 with the microplate support 4 and on the detection axis 24. The measuring head 2, i.e. the optical measuring/detection device, is also arranged on the detection axis 24, but above the moving unit 5 with the microplate support 4. The individual optical elements 2,2',2',2''' are preferably connected by means of fiber optics to each other, which is schematically indicated here by dot-dash and dashed lines (without necessarily representing the best or actual connection path).

A downwardly folding door 20 was opened for extending the moving unit 5 with the microplate support 4 from the housing 3 of the microplate reader 1. Instead of a downwardly folding door 20 it is also possible to provide a laterally displaceable door 20 for example (not shown). This alternative arrangement of the open door 20 facilitates receiving a microplate to be processed from a transfer station 37 positioned in front of the door 20 (see FIG. 11). This alternative arrangement of the open door 20 also supports the delivery of an already processed microplate to the transfer station 37 which is positioned in front of the door 20 (see FIG. 11). A further alternative arrangement of the open door is that the door 20 arranged as a flap will inwardly retract beneath the plate transport for opening. The placement of the microplate 8 on the microplate support 4 or the receiving of the magnet 8 from the microplate support 4 can occur (as illustrated) by a robot 18 equipped with gripper fingers 19 or also manually.

In a first alternative embodiment, the lid holding apparatus 6 can be arranged as a suction cup lifter 6" (not shown) and comprises at least one suction cup 14 which can be connected to a vacuum source 13. Said vacuum source 13 is preferably arranged in the housing 3 of the microplate reader 1. It can also be arranged outside of the microplate reader 1 due to lack of available space for example. In a second alternative embodiment, the lid holding apparatus 6 can be arranged as a gripper 6''' (not shown) and comprises at least two gripper fingers 15 for application to the lateral surfaces 16 of a microplate lid 7.

According to a preferred embodiment, the lid holding apparatus 6 is arranged to perform a lifting and lowering movement. According to an alternative embodiment, the lid holding apparatus 6 is arranged immovably in a stationary fashion. In this case however the moving unit 5 must be arranged to perform a lifting and lowering movement of the microplate support 4.

According to a similarly preferred embodiment, the optical measuring/detection device 2, i.e. the measuring head 2, is immovably arranged in a stationary fashion. It is also preferred to arrange the moving unit 5 to perform movements of the microplate support 4 in the X, Y, and Z directions of a Cartesian system of coordinates.

Figure 2:
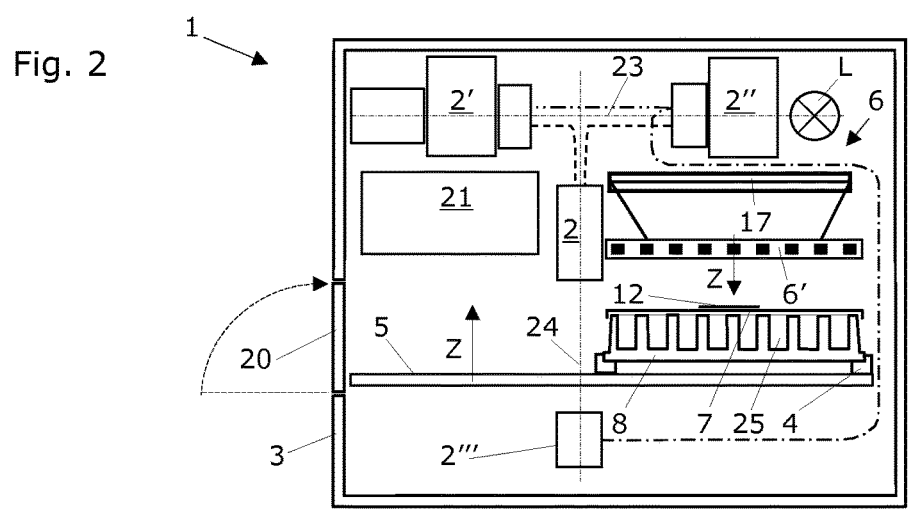
Figure 3:
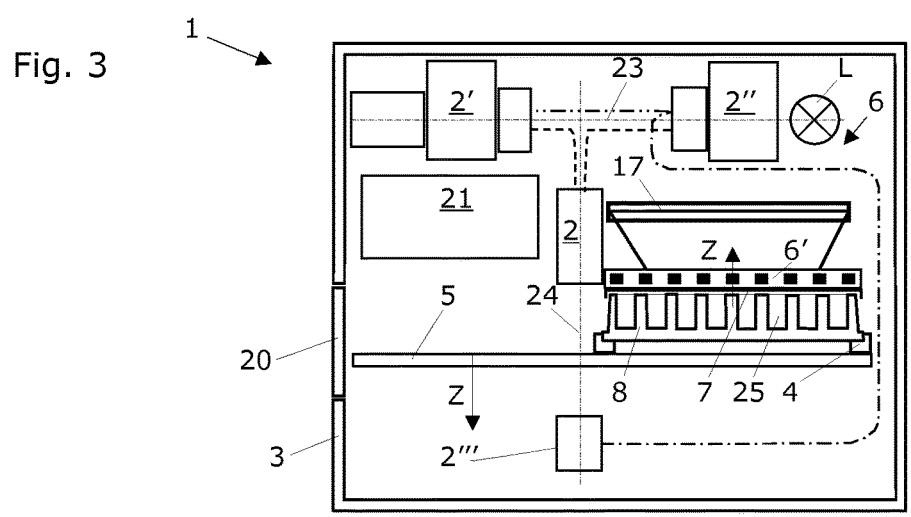
Figure 4:
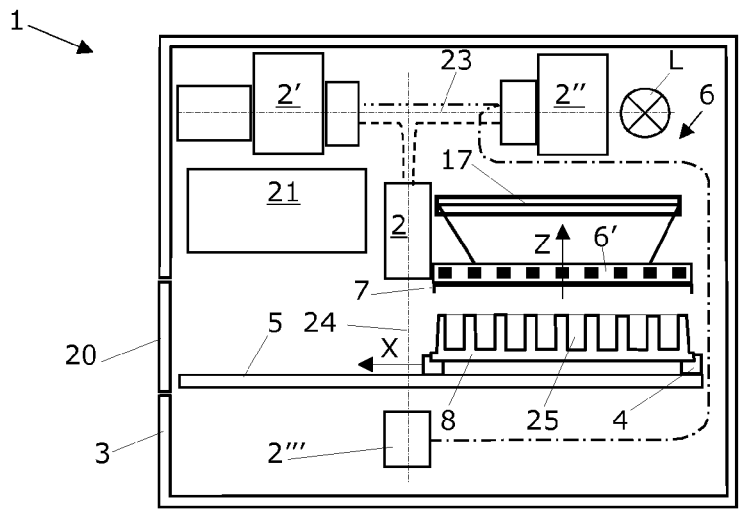
Figure 5:
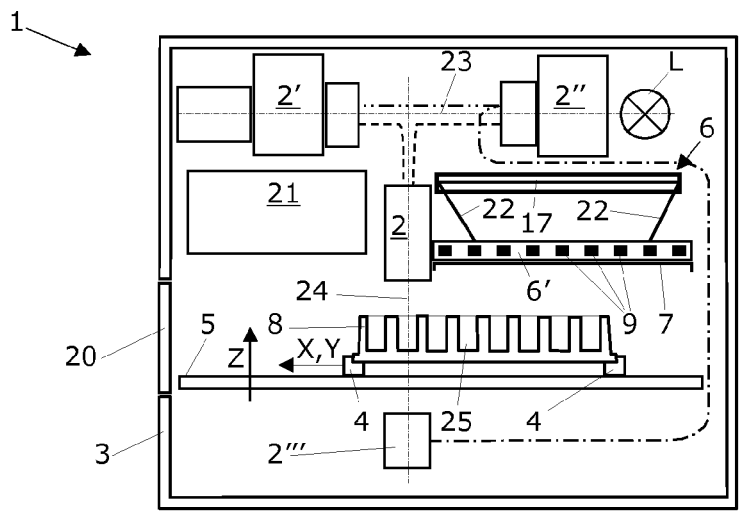
Figure 6:
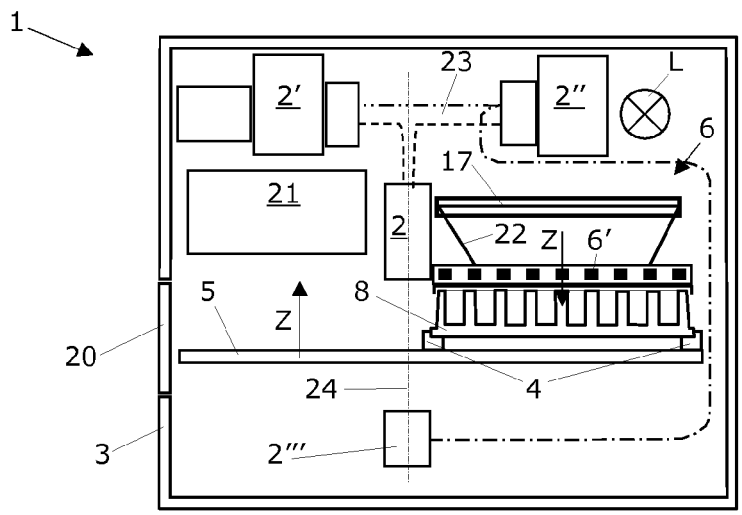
Figure 7:
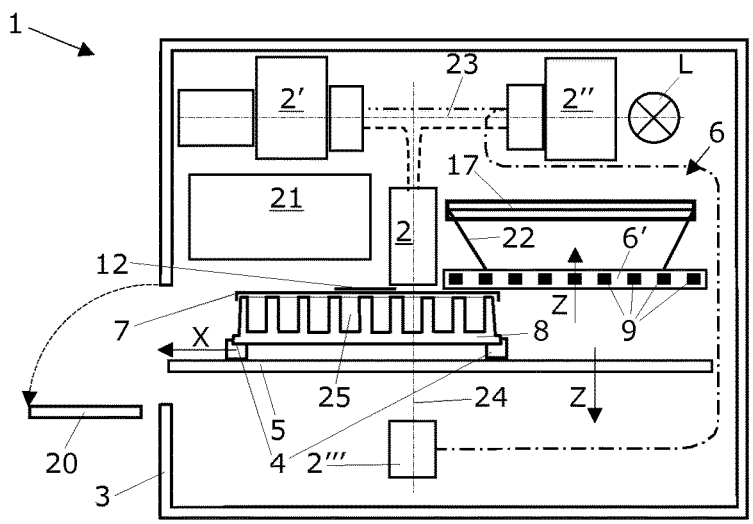
Figure 8:
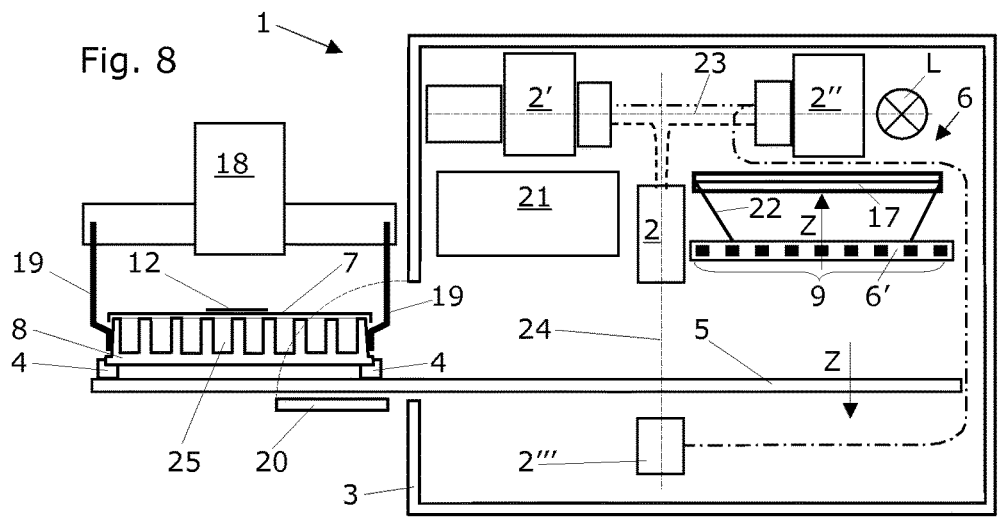

An exemplary method for optical measuring of samples in wells of a microplate 8 provided with a microplate lid 7 in a microplate reader 1 will now be explained in closer detail by reference to FIGS. 1 to 8. This method for measuring a microplate 8 will preferably be performed in a microplate reader 1 which comprises at least one optical measuring/detection device 2, a housing 3, a microplate support 4 and a moving unit 5. Preferably, the moving unit 5 is arranged to move the microplate support 4 out of the housing 3, into the housing 3 and, within the housing 3, in at least a substantially horizontal X direction. The method in accordance with the invention is characterized in that it comprises the following steps:

a) The placement of a microplate 8 covered by a microplate lid 7 on the microplate support 4 of the microplate reader 1. This is currently occurring in FIG. 1. The door 20 of the microplate reader 1 is preferably large enough that all possible microplate formats can be inserted by the moving unit 5 into the microplate reader 1.

b) The microplate support 4 and the covered microplate 8 are drawn by the moving unit 5 into the housing 3 of the microplate reader 1. This was just completed in FIG. 2 and the door 20 is closed. Preferably, all built-in parts of the microplate reader 1 are arranged to such an extent above the moving unit 5 and the microplate support 4 that all possible microplate formats can be moved by the moving unit 5 in the microplate reader 1.

c) The lifting of the microplate lid 7 from the microplate 8 positioned on the microplate support 4 by means of a lid holding apparatus 6 integrated in the microplate reader 1 and arranged within the housing 3 is prepared in FIG. 2 in that the microplate support 4 with the still covered microplate 8 is positioned in the receiving area of the lid holding apparatus 6. The lid holding apparatus 6 is subsequently lowered and/or the moving unit 5 is lifted with the microplate support 4 until the lid holding apparatus 6 comes into contact with the microplate lid 7, which is the case in FIG. 3. This establishment of contact is ensured in this case by means of a magnetizable material 12, which has been applied to the microplate lid 7 by way of example in form of a self-adhesive iron foil (see FIG. 1). Finally, the lid holding apparatus 6 is lifted and/or the moving unit 5 is lowered with the microplate support 4, so that the microplate 8 without the microplate lid 7 is ready for optical measurement of the samples in the wells 25 (see FIG. 4). As an alternative to the illustrated procedure with a lid holding apparatus 6 arranged as a magnetic lifter 6', the microplate lid 7 can be lifted by a lid holding apparatus 6 which is arranged as a suction cup lifter 6" or as a gripper 6'''.

d) The optical measurement of the microplate 8 with lifted microplate lid 7 by the at least one optical measuring/detection device 2 now occurs after the step-by-step displacement of the microplate 8 in the substantially horizontal X direction and Y direction, wherein each well 25 to be measured is moved into the detection axis 24 of the microplate reader 1. The optimal working distance between the microplate 8 and the measuring head 2 can be set by moving the microplate 8 and/or the measuring head 2 in a substantially vertical Z direction (see FIG. 5). The microplate lid 7 can be held during the measurement of the microplate 8 by the lid holding apparatus 6 within the housing 3 of the microplate reader 1 or be placed within the housing 3.

e) The replacement of the microplate lid 7 on the microplate 8 positioned on the microplate support 4 occurs by using the lid holding apparatus 6 integrated in the microplate reader 1 (see FIG. 6). For this purpose, the microplate 8 and the lid holding apparatus 6 are moved against each other in such a way that the microplate lid 7 is correctly placed on the microplate 8. In the case of the current use of a magnetic lifter 6' with a preferred array of permanent magnets 9 as a lid holding apparatus 6 and with a self-adhesive iron foil 12 on the microplate lid 7, the microplate lid 7 will be separated from the lid holding apparatus 6 in such a way that the microplate 8 with the microplate lid 7 placed thereon is horizontally displaced by the moving unit 5 (see FIG. 7). The microplate lid 7 will be stripped off from the bottom side of the lid holding apparatus 6 in this manner and will come to lie on the microplate 8.

f) The door 20 is opened again for the purpose of extending the microplate support 4 and the covered microplate 8 by the moving unit 5 from the housing 3 of the microplate reader 1 (see FIG. 8). The covered microplate 8 can be lifted from the extended microplate support 4 by means of a robot 18 equipped with gripper fingers 19 or by hand. The positioning of the microplate 8 on a transfer station 37 is also possible (see FIG. 11), from where it can be removed by means of the already described robot 18 or any other tool of any other laboratory implement that is suitable for this purpose.

A measuring method is also preferred in which the samples in the wells 25 of the microplate 8 are subjected to air and/or a reactant for triggering luminescence or other reactions between the lifting of the microplate lid 7 from the microplate 8 positioned on the microplate support 4 according to step c) and the optical measurement of the microplate 8 with lifted microplate lid 7 by the at least one optical measuring/detection device 2 according to step d).

The lifting and replacement of the microplate lid 7 in accordance with the invention in the interior of the microplate reader 1 (optionally in combination with a sample space arranged as a climatic chamber in the interior of the microplate reader 1) allows the performance of long-term tests and the monitoring of long-term kinetics (e.g. growth) of cell cultures in the wells 25 of microplate 8.

The optical measurements on the samples to be performed sporadically and repeatedly are enabled by brief lifting and replacement of the microplate lid 7. Similarly, the addition of culture medium or other substances and agents to the cell cultures in the wells 25 of microplate 8 is enabled by brief lifting and replacement of the microplate lid 7. Such long-term tests are preferably performed in standalone microplate readers 1.

As is shown in FIGS. 1 to 8, it is preferable in the described measuring method that the microplate lid 7 is placed on the microplate 8 after the optical measurement of the microplate 8 by using the lid holding apparatus 6 within the housing 3 of the microplate reader 1, and the microplate support 4 and the covered microplate 8 are conveyed by the moving unit 5 out of the housing 3 of the microplate reader 1.

Figure 9A:
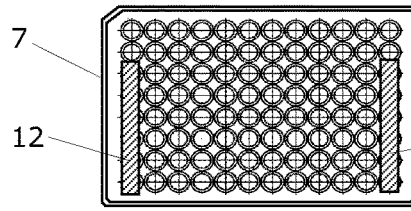
FIG. 9B shows two randomly positioned, at least approximately triangular pieces on the lid for a 24 well microplate.
FIG. 9C shows two randomly positioned pieces on the lid for a 6 well microplate, which pieces are placed between the wells and are approximately square.
FIG. 9D shows two alternatives of at least approximately rectangular pieces on the lid for a random standard microplate.
Figure 9B:
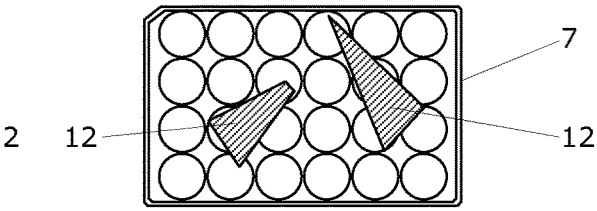
Figure 9C:
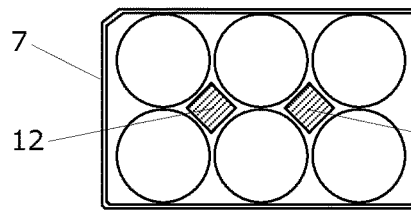
Figure 9D:
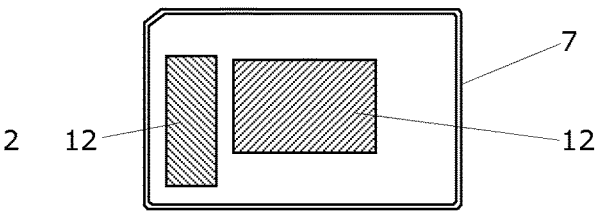

FIGS. 9A to 9D show top views of standard microplate lids 7 modified by a self-adhesive iron foil 12. The magnetizable material 12 can almost be formed at will as a result of using an array of permanent magnets 9 and can nearly be arranged as required. The examples of the attachment of a self-adhesive iron foil 12 as shown in FIGS. 9A, 9B, 9C and 9D provide perfect lifting and replacement of the microplate lid 7 without exception, wherein:

- two narrow, transverse and extremely positioned strips 12 were glued onto the lid 7 for a 96 well microplate (see FIG. 9A);
- two randomly positioned, at least approximately triangular pieces 12 were glued onto the lid for a 24 well microplate (see FIG. 9B);
- two randomly positioned, at least approximately square pieces 12 were glued onto the lid 7 for a 6 well microplate (see FIG. 9C);
- two alternatives of at least approximately rectangular pieces 12 were glued onto the lid 7 for a random standard microplate (see FIG. 9D).

The use of such a preferred array of permanent magnet 9 solves the problem of spontaneous displacement of the microplate lid 7 during lifting from the microplate 8. Such displacement can occur especially when the magnetic lifter 6' of the lid holding apparatus 6 is equipped with only one single permanent magnet or electromagnet, when this magnet has a substantially smaller area than the microplate lid 7 to be received, and when the magnetizable material 12 on or in the microplate lid 7 has a similar area as the magnet but is arranged in projection offset to the magnet. If in such a case the lid holding apparatus 6 with the magnetic lifter 6' approaches the microplate lid 7 to be lifted, this microplate lid 7 will be subjected to spontaneous horizontal displacement according to the horizontal displacement of the magnetizable material 12 in relation to the individual magnet of the magnetic lifter 6'. It is obvious that such a displaced microplate lid 7 can no longer be correctly replaced on the microplate 8 in an automated fashion. This displacement problem can be solved on the one hand in such a way that (as illustrated) an array of permanent magnets 9 is preferably used instead of the individual magnet. On the other hand, this displacement problem can be solved in such a way that the individual magnet of the magnetic lifter 6' and the magnetizable material 12 are mounted precisely on top of one another in projection.

A further possibility to solve this displacement problem is that the lid holding apparatus 6 comprises a plate made of a magnetizable material (e.g. of iron, nickel cobalt, or a metallic alloy comprising at least one of these metals) instead of the magnetic lifter 6', wherein this plate preferably has a surface which is larger than the surface of the microplate lid 7 to be received (not shown). The fixing of a magnetic material (e.g. a magnetic foil or an individual permanent magnet) on the microplate lid (not shown) will then be sufficient for example. Similarly, the lid holding apparatus 6 may comprise a magnetizable material 12 which is selected from a group which comprises self-adhesive metal foils, applied metallic lacquers, insert-molded metallic chips or metallic grains, and metal plates or metal foils that are inserted-molded or back-molded with plastics.

An even further possibility to solve this displacement problem is that the lid holding apparatus 6 comprises nonlinear non-array arrangements or distributions of at least three permanent magnets or of at least three electro magnets (see FIG. 12).

FIG. 10 shows a 3D view of the moving unit 5 with a microplate 8, whereon the microplate lid 7 with side surfaces 16 and a magnetizable material 12 is placed, positioned on the microplate support 4. The Cartesian system of coordinates is indicated by the three arrows (X, Y and Z). The moving unit 5 comprises two parallel guide rods 27, on which one respective slide bearing 30 is arranged. These two slide bearings 30 are connected to each other via a carriage 36. A first motor 26 moves said carriage 36 in an X direction of a Cartesian system of coordinates with a first toothed belt guided over a first deflection pulley 29. The microplate support 4 is fixed to the said carriage 36 by means of a link 33, wherein said link 33 is movably guided along a linear guide 32 and along the carriage 36. A second motor 31 moves the link 33 with the microplate support 4 in a Y direction of the Cartesian system of coordinates by means of a second toothed belt 34 which is guided via a second deflection pulley 35. The moving device 5 as described above is preferably movable in a Z direction of the Cartesian system of coordinates (not shown in FIG. 10).

FIG. 10 further shows a lid holding apparatus 6 with a magnetic lifter 6', which comprises a single switchable permanent magnet 11 according to a first variant of a second embodiment. Switchable permanent magnets are known from the state of the art (cf. EP 0 114 259 B1 for example) and will be adjusted by a person skilled in the art with knowledge of the present invention in its construction and arrangement to the requirements for lifting a microplate lid 7.

According to the first variant of the second embodiment of the lid holding apparatus 6 with a magnetic lifter 6', the single switchable permanent magnet 11 preferably is located and movable within a support 42 in approximately vertical direction. The single switchable permanent magnet 11 thus can be lowered and lifted in relation to the support 42. This support 42 is a part of or is attached to the carrying apparatus 17 of the microplate reader 1. The support 42 may carry a crank 41 for guided taking-up a microplate lid 7 from a microplate 8 that is positioned on the microplate support 4. This guided taking-up results in keeping the microplate lid 7 aligned in a precise location within the crank 41 and save holding of the microplate lid 7 with the single switchable permanent magnet 11 of the lid holding apparatus 6. Thanks to keeping the microplate lid 7 aligned by the crank 41 of the lid holding apparatus 6, the microplate lid 7 is guided during setting-down and thus can be exactly positioned on top of the microplate 8 that is positioned on the microplate support 4. The microplate 8 on which the microplate lid 7 is set down can be the same microplate 8 from which the microplate lid 7 had been lifted earlier or another microplate 8.

Instead of utilizing a combination of one single switchable permanent magnet 11 and a crank 41 for lifting a microplate lid 7 and according to a second variant of the second embodiment of the lid holding apparatus 6 with a magnetic lifter 6', a pair of switchable permanent magnets 11 can be used (see FIGS. 13 to 17).

Utilizing a combination of two switchable permanent magnets 11 and a crank 41 is also preferred.

Instead of the lid holding apparatus 6 with a magnetic lifter 6', a person skilled in the art, with knowledge of the present invention, can easily provide a lid holding apparatus 6 which is arranged as a suction cup lifter 6" or as a gripper 6''', wherein said person would coordinate any required lifting and lowering movement of the lid holding apparatus 6 with the movements of the moving unit 5 for performing movements of the microplate support 4 in the X, Y and Z directions of a Cartesian system of coordinates.

FIG. 11 shows a slightly enlarged 3D view of the empty microplate support 4 of the moving unit 5 (according to FIG. 10) at a transfer station 37 and in the respective enlargement a 3D view of a 96 well microplate 8 without the microplate lid 7. The transfer station 37 comprises a support plate 38 of a shape adjusted to the microplate support 4, wherein the microplate support 4 comprises cut-outs 39 which protrude beyond the footprint 40 of a standard microplate 8, so that parts of the sup-port plate 38 which protrude into these cut-outs 39 are sufficient for carrying the microplate 8.

The microplate support 4 of the moving unit 5 is extended for receiving a microplate 4 at the transfer station 37 in a Z level which is situated beneath the level of the support plate 38 of the transfer station 37 and therefore also beneath the footprint 40 of the microplate 8 of said support plate 38. After assuming a correct transfer position, the microplate support 4 is lifted in the Z direction until the microplate 8 rests on the microplate support 4. At the same time, the large cut-out 39 in the support plate 38 (at the bottom in FIG. 11) enables the transfer station 37 to be approached at a lower level than the surface of the support plate if said support plate 38 is to be supported by a central pillar (not shown) on a working surface of a laboratory workstation (not shown).

For the purpose of delivering the microplate 4 at the transfer station 37, the microplate support 4 of the moving unit 5 will be extended in a Z level which is situated above the level of the support plate 38 of the transfer station 37. After assuming a correct transfer position, the microplate support 4 is lowered in the Z direction until the microplate 8 rests on the support plate 38 of the transfer station 37.

FIG. 12 shows examples of non-array arrangements of three permanent magnets 9' and four electro magnets 10' in relation to the area of a preferred magnetizable material 12 that is attached to a microplate lid 7. Preferably, the magnetizable material 12 is a circular iron disc with a diameter of 50 mm and a thickness of 0.5 mm. It is particularly preferred to degrease this iron plate with a non-back-greasing means (e.g. isopropanol) and then to attach this iron plate to a clean top surface of a microplate lid 7 by means of a pressure-sensitive double-sided tape (e.g. 3M 9485, 3M Deutschland GmbH, 41453 Neuss, Germany) by pressing with a roller applying a minimal pressure of 20 N/cm². It is preferred to attach the circular iron disc in the middle of the microplate lid surface as shown.

The magnetic lifter 6' may comprise at least three permanent magnets 9' or electro magnets 10' that are arranged in a non-array arrangement situated within the area of such an iron disc. If an iron or other magnetizable metal disc of greater or smaller diameter is used the distances between the at least three permanent magnets 9' or electro magnets 10' may be greater or smaller as well. Depending on the actual size of the permanent magnets 9' or electro magnets 10' chosen and depending on the circular or non-circular area of the magnetizable material, more than three permanent magnets 9' or electro magnets 10' may be appropriately positioned within an area in the magnetic lifter 6' that is similar to or even a bit smaller than the circular or non-circular area of the magnetizable material 12 on the microplate lid 7.

FIG. 13 shows a vertical sectional view through a microplate reader 1 with retracted moving unit 5 and microplate support 4, prior to the lifting of the microplate lid 7 with an integrated lid holding apparatus 6 according to a second variant of a second embodiment (compare with FIG. 2). Instead of utilizing a combination of one single switchable permanent magnet 11 and a crank 41 for lifting a microplate lid 7 according to the first variant of the second embodiment (see FIG. 10) and according to this second variant of the second embodiment of the lid holding apparatus 6 with a magnetic lifter 6', a pair of switchable permanent magnets 11 are used. Utilizing a combination of two switchable permanent magnets 11 and a crank 41 is also preferable. The two switchable permanent magnets 11 are horizontally aligned such that they entirely are located within the circular or non-circular area of the magnetizable material 12 on the microplate lid 7. Because the two switchable permanent magnets 11 are aligned in a direction that runs perpendicular to the longitudinal axis of a microplate lid 7 (compare FIG. 12), only one switchable permanent magnet 11 is visible here. This arrangement of a pair of switchable permanent magnets 11 also solves the above discussed displacement problem between the microplate lid 7 that is attached to the lid holding apparatus 6 and the microplate 8 that is positioned on the microplate support 4 of the microplate reader 1. As depicted here, the magnetic lifter 6' is movably arranged within a support 42 that is attached to carrying apparatus 17 inside the housing 3 of the microplate reader 1.

It also can be seen from FIG. 13, that a switchable permanent magnet 11 comprises one permanent magnet 9' and one electro magnet 10' that are mounted on top of each other. Preferably, such a combination of a single permanent magnet 9' and a single electro magnet 10' is utilized to build a single switchable permanent magnet 11. Especially preferred and approved are PE-Magnets of the type ITS-PE 1212-24VDC-TEC of M RED MAGNETICS® (Intertec Components GmbH, 85356 Freising, Germany). Such PE magnets are high quality permanent magnets that normally cultivate their holding force without electric current. The magnetism of the permanent magnet 9' is neutralized via activation of the associated electro magnet 10'.

The magnetic lifter 6' is depicted here in its uppermost position where there is no interaction of the two permanent magnets 9' of the magnetic lifter 6' with the magnetizable material 12 on the microplate lid 7. The two electro magnets 10' may be activated or not activated here.

FIG. 14 shows a vertical sectional view through a microplate reader 1 with retracted moving unit 5 and microplate support 4, during lifting of the microplate lid 7 with a magnetic lifter 6' of the integrated lid holding apparatus 6 (compare with FIG. 3) according to the second embodiment (see FIG. 13).

The magnetic lifter 6' is depicted here in its lowermost position where there is interaction of the two permanent magnets 9' of the magnetic lifter 6' with the magnetizable material 12 on the microplate lid 7. Depending on the status of the two electro magnets 10', the magnetizable material 12 on the microplate lid 7 is:

attracted by the permanent magnets 9' if the electro magnets 10' are not activated, or is not attracted by the permanent magnets 9' if the electro magnets 10' are activated.

Thus, the depicted situation for the start of moving the microplate lid 7 away from the microplate 8 and for the end of replacing the microplate lid 7 on top of the microplate 8 is the same. However as said, the actual action is depending on the status of the two electro magnets 10':

Moving the magnetic lifter 6' into its uppermost position (compare with FIG. 13) while the two electro magnets 10' are not activated results in moving the microplate lid 7 away from the microplate 8; such moving away can be supported by lowering the microplate 8 through lowering the microplate support 4 (compare with FIG. 11). Accordingly, a power fail that deactivates the electro magnets 10' does not result in losing the microplate lid 7 from the magnetic lifter 6'; in consequence, a microplate lid 7 is safely hold by the magnetic lifter 6' even in case of an electric outage or power failure.

Moving the magnetic lifter 6' again into its lowermost position (compare with FIG. 14) while the two electro magnets 10' are not activated results in replacing the microplate lid 7 on top of the microplate 8; such re-covering the microplate 8 can be supported by lifting the microplate 8 through lifting the microplate support 4 (compare with FIG. 11).

For releasing the microplate lid 7 from the magnetic lifter 6' on top of the microplate 8, the two electro magnets 10' are activated which results in a magnetic field that is inverse to the magnetic field of the permanent magnets 9'. Subsequently, the magnetic lifter 6' is moved to its uppermost position with (at least initially) activated electro magnets 10' (see FIG. 13).

FIG. 15 shows a vertical section view of the magnetic lifter 6' of the integrated lid holding apparatus 6 according to the second version of the second embodiment. The section plane A-A is indicated in FIG. 16 and runs perpendicular to the longitudinal axis of the microplate lid 7 to be moved and hold. Inside a support 42 there is located a vertical linear guide rail 32' on which a wagon 45 is movable in Z direction, i.e. vertically. This wagon 45 is operably connected with a drive 43 located at the top of the support 42. The drive 42 is embodied here as a linear actuator. Attached to the wagon 45 is a magnet holder 46 which carries two switchable permanent magnets 11 (i.e. PE-Magnets of the type ITS-PE 1212-24VDC-TEC of M RED MAGNETICS® of Intertec Components GmbH, 85356 Freising, Germany). The diameter of the preferred PE-Magnets is 12 mm and their axial distance preferably is 20 mm as indicated in FIG. 15. The vertical movement of the wagon and PE-Magnets may be monitored and controlled e.g. via an optical fork sensor 49 that is attached to the support 42 and a cam switch 50 attached to the wagon 45.

Around the switchable permanent magnets 11 there preferably is located a friction overlay support 48 which carries a friction overlay 47. Utilizing such a friction overlay 47 in addition to the pair of switchable permanent magnets 11 enhances protection of the lid 7 against unwanted movements and thus leaving a defined position when attracted to the magnetic lifter 6'. Especially when vibrations occur to the microplate reader 1 or when the microplate reader 1 itself produces vibrations during the time a microplate lid 7 is lifted from a microplate 8. Such vibrations may be produced for example during shaking a microplate that is e.g. carried out in order to mix reagents and samples in wells 25 of the microplate 8.

FIG. 16 shows a side view of the magnetic lifter 6' of the integrated lid holding apparatus 6 according to the second version of the second embodiment. From the outside of the lid holding apparatus 6 which is still inside the housing 3 of the microplate reader 1, the support 42, the drive 43 for moving the magnetic lifter 6' in a Z direction, and the friction overlay carrier 48 with attached friction overlay 47 are visible. The support 42 may be fixed to the carrying apparatus 17 of the microplate reader 1 via a flange 51. The plane A-A for the section shown in FIG. 15 is indicated. Preferably as shown, the axis of the linear actuator drive 42 is identical with the axis of the magnet holder 46 and thus coaxial with the axis of the magnetic lifter 6'.

FIG. 17 shows a bottom view of the magnetic lifter 6' of the integrated lid holding apparatus 6 according to the second version of the second embodiment. This view is achieved when looking from the magnetizable material 12 on the microplate lid 7 in vertical direction (i.e. in direction of the vertical axis 52 of the magnetic lifter 6') against the lid holding apparatus 6. In this case, an iron plate with 50 mm diameter is indicated, the center of which being penetrated by the vertical axis 52 of the magnetic lifter 6'. The two switchable permanent magnets 11 are arranged as indicated in FIG. 15; this results in an area of 37 mm by 17 mm that is covered by the oval formed friction overlay 47 which essentially runs as a strip around the two switchable permanent magnets 11. Also visible are the vertical linear guide rail 32', the wagon 45 for the magnetic lifter 6', the friction overlay support 48, the optical fork sensor 49, the cam switch 50, and the flange 51.

It is clear from this FIG. 17 that with this dimension of the friction overlay 47 (oval of 37 mm by 17 mm) and with this dimension of the magnetizable material 12 (circular disc with 50 mm diameter) there is some tolerance allowed with regard to the mutual positioning of the center of the magnetizable material 12 and the vertical axis 52 of the magnetic lifter 6'. In order to always guarantee full contact over the entire area of the friction overlay 47 with the disc-shaped magnetizable material 12, the maximal tolerance is +/−6.5 mm. Preferably, the two switchable permanent magnets 11 are thus arranged at a distance that is smaller than a width of the microplate lid 7 to be moved away from the microplate 8.

Preferably, the magnetic lifter 6' is moved by a spindle of the linear actuator drive 42 to a certain position over (and to a distance to) the microplate lid 7 to be lifted. This distance preferably is chosen such that regardless of different heights of microplates 8 present and/or the actual Z-level of a microplate lid 7 to be lifted, always the same Z-level can be approached (monitored and controlled by the optical fork sensor 49).

In one preferred embodiment, the magnetic lifter 6' comprises a single permanent magnet 9' or at least three permanent magnets 9' located in a non-array arrangement. In this preferred embodiment on the one hand, the magnetic lifter 6' may comprise a crank 41 with four sides, three sides being equipped with a guiding flank for guided taking-up a microplate lid 7 from a microplate 8, and one side being void of a guiding flank, thus enabling a microplate lid 7 held by at least one permanent magnet 9' to be stripped off from the crank 41 on the side without guiding flank and to come to lie on a microplate 8 that is positioned on the microplate support 4. In this preferred embodiment on the other hand, the magnetic lifter 6' comprises a support 42 that is attached to a carrying apparatus 17 of the microplate reader 1, said single permanent magnet 9' or non-array arrangement of at least three permanent magnets 9' being movable within the support 42 in approximately vertical direction. All elements in this preferred embodiment may be combined.

In another preferred embodiment, the magnetic lifter 6' comprises one single switchable permanent magnet 11, or at least three electro magnets 10' or switchable permanent magnets 11 located in each case in a non-array arrangement. In this preferred embodiment on the one hand, the magnetic lifter 6' comprises a crank 41 with four sides that all are equipped with a guiding flank for guided taking-up a microplate lid 7 from a microplate 8, thus enabling a microplate lid 7 held by at least one switchable permanent magnet 11 or at least three electro magnets 10' to be dropped off from the crank 41 and to come to lie on a microplate 8 that is positioned on the microplate support 4. Such dropping e.g. is enabled by switching off the electromagnets or by activating the electro magnet in the switchable permanent magnets 11. In this preferred embodiment on the other hand, the magnetic lifter 6' comprises a support 42 that is attached to a carrying apparatus 17 of the microplate reader 1, said single switchable permanent magnet 11, non-array arrangement of at least three electro magnets 10' or switchable permanent magnets 11 being movable within the support 42 in approximately vertical direction. All elements in this preferred embodiment may be combined.

In a particularly preferred embodiment, the magnetic lifter 6' comprises two switchable permanent magnets 11 that are mounted to a magnet holder 46. In this preferred embodiment on the one hand, the magnetic lifter 6' comprises a friction overlay 47 thus enabling a microplate lid 7 to be safely held by the two switchable permanent magnets 11, hindered from unwanted movements by the friction overlay 47 and to be dropped off from the magnetic lifter 6' and to come to lie on a microplate 8 that is positioned on the microplate support 4. In this preferred embodiment on the other hand, the magnetic lifter 6' comprises a support 42 that is attached to a carrying apparatus 17 of the microplate reader 1, said two switchable permanent magnets 11 being movable within the support 42 in approximately vertical direction. Preferably, the two switchable permanent magnets 11 are arranged at a distance that is smaller than a width of the microplate lid 7 to be moved away from the microplate 8 (see FIGS. 12-17). All elements in this preferred embodiment may be combined.

In the context of the present invention, each switchable permanent magnet 11 preferably is configured as:
- a combination of a stationary permanent magnet 9' and a stationary electro magnet 10', or
- a combination of a stationary permanent magnet 9' and a movable permanent magnet 9' that are mechanically superimposable by angular or linear displacement, or
- a combination of a stationary permanent magnet 9' and a mechanically movable magnet shield, or
- a combination of a stationary magnet shield and a mechanically movable permanent magnet 9'.

FIGS. 18A and 18B show top views of standard microplate lids 7 modified with self-adhesive iron foil utilized as magnetizable material 12. FIG. 18A shows on the lid 7 for a 96 well microplate 8 two identical, transversely disposed strips of magnetizable material 12, each configured to interact with two permanent magnets 9'. This variant of utilizing magnetizable material 12 is preferred because it is easy to attach the strips in a place that at least nearly is optimal when considering the projected areas of the permanent magnets 9' indicated by circles.

FIG. 18B shows on the lid for a 24 well microplate two transversely positioned, at least approximately triangular pieces of magnetizable material 12 configured to interact with one or two electro magnets 10'. The electro magnets 10' are placed at the same locations as the permanent magnets 9' in FIG. 8A. This variant of utilizing magnetizable material 12 demonstrates that it is sufficient if the projected area (circles) of at least one electro magnet 10' lays within the physical area of a magnetizable material 12 in each case.

FIGS. 19A and 19B show a horizontal section view through a crank 41 of a magnetic lifter 6' and a top view of a microplate lid 7 safely held in this crank 41 in a precise location. FIG. 19A shows a crank 41 comprising two guiding flanks 53 that are building a corner where they meet each other. A microplate lid 7 with a centrally positioned magnetizable material 12 configured to interact with two electro magnets 10' or switchable permanent magnets 11 is shown here. The two electro magnets 10' or switchable permanent magnets 11 are arranged peripherally with respect to the physical area of the magnetizable material 12. Peripheral orientation of at least one electro magnet 10' or switchable permanent magnet 11 results in attracting the magnetizable material 12 and drawing the microplate lid 7 against the corner built by the two guiding flanks 53 when the magnetic lifter 6' and the microplate lid 7 are mutually approaching for lifting the microplate lid 7 off a microplate 8.

FIG. 19B shows a crank 41 comprising two guiding flanks 53 that are not touching each other but nevertheless building an imaginary corner. A microplate lid 7 with a centrally positioned magnetizable material 12 configured to interact with two permanent magnets 9' is shown here. The two permanent magnets 9' are arranged peripherally with respect to the physical area of the magnetizable material 12. Peripheral orientation of at least one permanent magnet 9' also here results in attracting the magnetizable material 12 and drawing the microplate lid 7 against the imaginary corner defined by the two guiding flanks 53 when the magnetic lifter 6' and the microplate lid 7 are mutually approaching for lifting the microplate lid 7 off a microplate 8.

FIGS. 20A and 20B show a horizontal section view through a crank 41 of a magnetic lifter 6' and a top view of a microplate lid 7 safely held in this crank 41 in a precise location. FIG. 20A shows a crank 41 comprising one guiding flank 53 and one guiding pin 54 that are defining an imaginary corner. A microplate lid 7 with a peripherally positioned magnetizable material 12 configured to interact with one permanent magnet 9' is shown here. The permanent magnet 9' is peripherally arranged with respect to the physical area of the magnetizable material 12. Peripheral orientation of this at least one permanent magnet 9' results in attracting the magnetizable material 12 and drawing the microplate lid 7 against the imaginary corner defined by the guiding flank 53 and the guiding pin 54 when the magnetic lifter 6' and the microplate lid 7 are mutually approaching for lifting the microplate lid 7 off a microplate 8.

FIG. 20B shows a crank 41 comprising two guiding pins 54 on two sides that are defining an imaginary corner. A microplate lid 7 with a peripherally positioned magnetizable material 12 configured to interact with one electro magnet 10' or switchable permanent magnet 11 is shown here. The electro magnet 10' or switchable permanent magnet 11 is peripherally arranged with respect to the physical area of the magnetizable material 12. Peripheral orientation of this at least one electro magnet 10' or switchable permanent magnet 11 results in attracting the magnetizable material 12 and drawing the microplate lid 7 against the imaginary corner defined by the guiding pins 54 when the magnetic lifter 6' and the microplate lid 7 are mutually approaching for lifting the microplate lid 7 off a microplate 8.

It is especially preferred that the comprises magnetizable material (12) with a physical area, a projected area of the at least one permanent magnet (9'), electro magnet (10'), or switchable permanent magnet (11) being smaller than the physical area of the magnetizable material (12) of the microplate lid (7). Or with other words, it is particularly preferred that wherein a microplate lid (7) utilized for carrying out the method comprises magnetizable material (12) with a physical area that is at least double the projected area of the at least one permanent magnet (9'), electro magnet (10'), or switchable permanent magnet (11) of the magnetic lifter (6').

All described or shown examples of magnetizable material 12 on or in a microplate lid 7 clearly show a physical area that is at least double the projected area of the at least one permanent magnet 9', electro magnet 10', or switchable permanent magnet 11 of the magnetic lifter 6' (see e.g. FIG. 17). Thus even using only one permanent magnet 9', electro magnet 10', or switchable permanent magnet 11 offers the same advantage as using an array of permanent magnets 9 or an electromagnetic array 10, because there is no need of exact positioning the physical area of the magnetizable material 12 of a microplate lid 7 with respect to the projected area of the at least one permanent magnet 9', electro magnet 10', or switchable permanent magnet 11 of the magnetic lifter 6'.

In order to enable the magnetic lifter 6' that is equipped with at least one of a permanent magnet 9', electro magnet 10', or switchable permanent magnet 11 for guided taking-up and setting-down a microplate lid 7, the magnetic lifter 6' preferably is comprising a crank 41 that is configured for keeping the microplate lid 7 aligned in a precise location within the crank 41.

Each skilled person, when knowing the present invention, is able to carry out and/or implement one, or another, or even a combination of these configurations of one or more switchable permanent magnets 11 for exploiting the present invention.

A combination of selected elements of a single embodiment or of two or more embodiments disclosed herein belongs to the present invention.

The same reference numerals in the drawings designate the same or at least similar features, even if they are not described in detail in each case.

LIST OF REFERENCE NUMERALS

1 Microplate reader
2 Optical measuring/detection device, measuring head
2' Detection optics
2" First excitation optics
2''' Second excitation optics
3 Housing
4 Microplate support
5 Moving unit
6 Lid holding apparatus
6' Magnetic lifter
6" Suction cup lifter
6''' Gripper
7 Microplate lid
8 Microplate
9 Array of permanent magnets
9' Permanent magnet
10 Electromagnetic array
10' Electro magnet
11 Switchable permanent magnet
12 Magnetizable material
13 Vacuum source
14 Suction cup
15 Gripper finger of 6'''
16 Side surfaces of 7
17 Carrying apparatus
18 Robot
19 Gripper finger of 18
20 Door
21 Control unit
22 Flexible, pliable elements
23 Optical axis
24 Detection axis
25 Well of 8
26 First motor
27 Guide rod
28 First toothed belt
29 First deflection pulley
30 Slide bearing
31 Second motor
32 Horizontal linear guide
32' Vertical linear guide
33 Link
34 Second toothed belt
35 Second deflection pulley
36 Carriage
37 Transfer station
38 Support plate of 37
39 Cut-outs of 38
40 Footprint of 4
41 Crank
42 Support
43 Vertical drive for 6'
44 Vertical drive for 4
45 Wagon
46 Magnet holder
47 Friction overlay
48 Friction overlay support
49 Optical fork sensor
50 Cam switch
51 Flange
52 Vertical axis of 6'
53 Guiding flank
54 Guiding pin
L Light source

The invention claimed is:

1. A method for optically measuring in a microplate reader (1) samples in wells (25) of a microplate (8) provided with a microplate lid (7), wherein the microplate reader (1) comprises at least one optical measuring/detection device (2), a housing (3), a microplate support (4) and a moving unit (5), wherein the moving unit (5) is arranged to move the microplate support (4) out of the housing, into the housing (3) and in at least one horizontal direction within the housing (3), wherein the measuring method comprises the following steps:
(a) placing the microplate (8) covered by the microplate lid (7) on the microplate support (4) of the microplate reader (1), the microplate lid comprising magnetizable material;
(b) retracting the microplate support (4) and the covered microplate (8) by the moving unit (5) into the housing (3) of the microplate reader (1);
(c) moving the microplate lid (7) away from the microplate (8) positioned on the microplate support (4) with a lid holding apparatus (6) integrated in the microplate reader (1) and arranged within the housing (3), and (d) measuring samples in wells (25) of the microplate (8) with the lifted microplate lid (7) by the at least one optical measuring/detection device (2), wherein the lid holding apparatus (6) is arranged as a magnetic lifter (6') and comprises a non-array arrangement of at least one:

(i) permanent magnet (9'), or (ii) electro magnet (10'), or (iii) switchable permanent magnet (11), and wherein each microplate lid (7) to be moved away from the microplate (8) comprises magnetizable material (12) with a physical area; a projected area of the at least one permanent magnet (9'), electro magnet (10'), or switchable permanent magnet (11) being smaller than the physical area of the magnetizable material (12) of the microplate lid (7).

2. The method of claim 1, wherein a microplate lid (7) utilized for carrying out the method comprises magnetizable material (12) with a physical area that is at least double the projected area of the at least one permanent magnet (9'), electro magnet (10'), or switchable permanent magnet (11) of the magnetic lifter (6').

3. The method of claim 1, wherein moving the microplate lid (7) away from the microplate (8) is carried out by:

lifting the lid holding apparatus (6) with the microplate lid (7) in an at least approximately vertical direction away from the microplate (8), or lowering the microplate support (4) with the microplate (8) in an at least approximately vertical direction away from the lid holding apparatus (6) with the microplate lid (7), or lifting the lid holding apparatus (6) with the microplate lid (7) and lowering the microplate support (4) with the microplate (8) in an at least approximately vertical directions away from each other.

4. The method of claim 1, wherein the microplate lid (7) is replaced on the microplate (8) positioned on the microplate support (4) by using the lid holding apparatus (6) integrated in the microplate reader (1).

5. The method of claim 1, wherein the microplate support (4) and the covered microplate (8) are conveyed by the moving unit (5) out of the housing (3) of the microplate reader (1).

6. The method of claim 1, wherein the microplate lid (7) is held by the lid holding apparatus (6) within the housing (3) of the microplate reader (1) or placed in the housing (3) during the optical measurement of samples in wells (25) of the microplate (8).

7. The method of claim 1, wherein the samples in the wells (25) of the microplate (8) are brought into contact with air and/or a reagent for triggering luminescence or other reactions between the lifting of the microplate lid (7) from the microplate (8) positioned on the microplate support (4) according to step (c) and the optical measurement of samples in wells (25) of the microplate (8) with lifted microplate lid (7) is performed by the at least one optical measuring/detection device (2) according to step (d).

8. The curing method of claim 1, wherein the microplate lid (7) is placed on the microplate (8) within the housing (3) of the microplate reader (1) by using the lid holding apparatus (6) after the optical measurement of the samples in wells (25) of the microplate (8), and the microplate support (4) and the covered microplate (8) are conveyed by the moving unit (5) out of the housing (3) of the microplate reader (1).

9. The method of claim 1, wherein the microplate lid (7) is lifted and replaced several times during a long-term test, for the optical measurement of samples in wells (25) of the microplate (8) to occur.

* * * * *